United States Patent
Luginbuhl et al.

(10) Patent No.: US 7,908,690 B2
(45) Date of Patent: Mar. 22, 2011

(54) SUPINE PATIENT SUPPORT FOR MEDICAL IMAGING

(75) Inventors: Christopher Alexander Luginbuhl, Toronto (CA); Cameron Anthony Piron, Toronto (CA); Josh Richmond, Toronto (CA)

(73) Assignee: Sentinelle Medical, Inc., Toronto (CA)

( * ) Notice: Subject to any disclaimer, the term of this patent is extended or adjusted under 35 U.S.C. 154(b) by 0 days.

(21) Appl. No.: 12/124,558

(22) Filed: May 21, 2008

(65) Prior Publication Data

US 2008/0216239 A1    Sep. 11, 2008

Related U.S. Application Data

(63) Continuation-in-part of application No. 11/949,445, filed on Dec. 3, 2007, which is a continuation-in-part of application No. 10/916,738, filed on Aug. 12, 2004, now Pat. No. 7,379,769.

(60) Provisional application No. 60/931,542, filed on May 23, 2007, provisional application No. 60/872,345, filed on Dec. 1, 2006, provisional application No. 60/506,784, filed on Sep. 30, 2003.

(51) Int. Cl.
*A47B 13/00* (2006.01)
(52) U.S. Cl. .............. 5/601; 5/600; 600/415; 600/411
(58) Field of Classification Search .............. 5/600, 601; 600/411, 417, 426, 476, 415; 378/87
See application file for complete search history.

(56) References Cited

U.S. PATENT DOCUMENTS

| | | | |
|---|---|---|---|
| 4,503,844 A * | 3/1985 | Siczek | ............. 606/245 |
| 4,552,346 A | 11/1985 | Schnelle et al. | |
| 4,572,203 A | 2/1986 | Feinstein | |
| 4,825,162 A | 4/1989 | Roemer et al. | |
| 4,930,516 A | 6/1990 | Alfano et al. | |
| 4,943,986 A | 7/1990 | Barbarisi | |
| 4,989,608 A | 2/1991 | Ratner | |
| 5,072,721 A * | 12/1991 | Weiler et al. | ............. 601/4 |
| 5,154,179 A | 10/1992 | Ratner | |
| 5,426,685 A | 6/1995 | Pellegrino et al. | |
| 5,548,218 A | 8/1996 | Lu | |

(Continued)

FOREIGN PATENT DOCUMENTS

EP        0396866        11/1990

(Continued)

OTHER PUBLICATIONS

Cameron A. Piron, Hybrid Imaging Guidance System for Biopsy of the Breast, thesis paper, University of Toronto, 2001.

(Continued)

*Primary Examiner* — Robert G Santos
*Assistant Examiner* — Brittany M Wilson
(74) *Attorney, Agent, or Firm* — Quarles & Brady LLP

(57) ABSTRACT

A patient supporting apparatus used in medical imaging technologies has an inventive tabletop and stretcher system. The tabletop has a gap or narrowing of prescribed location and size, for example, more than thirty percent of the width of the tabletop is removed inferior to the patient's pelvis within a region of at least 0.3 meters in length. The stretcher supports the tabletop and includes a gap or narrowing so that the access of the operator's hand, arm, and line of sight is not obstructed from the gap or narrowing of the tabletop.

20 Claims, 10 Drawing Sheets

U.S. PATENT DOCUMENTS

| | | | |
|---|---|---|---|
| 5,590,653 A | 1/1997 | Aida et al. | |
| 5,590,655 A | 1/1997 | Hussman | |
| 5,594,337 A | 1/1997 | Boskamp | |
| 5,678,549 A | 10/1997 | Heywang-Koebrunner et al. | |
| 5,682,098 A | 10/1997 | Vij | |
| 5,682,890 A | 11/1997 | Kormos et al. | |
| 5,706,812 A | 1/1998 | Strenk et al. | |
| 5,744,958 A | 4/1998 | Werne | |
| 5,782,764 A | 7/1998 | Werne | |
| 5,855,554 A * | 1/1999 | Schneider et al. | 600/407 |
| 5,868,673 A | 2/1999 | Vesely | |
| 5,868,757 A | 2/1999 | Koutrovelis | |
| 5,944,023 A | 8/1999 | Johnson et al. | |
| 6,066,102 A | 5/2000 | Townsend et al. | |
| 6,091,985 A | 7/2000 | Alfano et al. | |
| 6,159,221 A | 12/2000 | Chakeres | |
| 6,163,616 A | 12/2000 | Feldman | |
| 6,163,717 A | 12/2000 | Su | |
| 6,174,291 B1 | 1/2001 | McMahon et al. | |
| 6,201,392 B1 | 3/2001 | Anderson et al. | |
| 6,295,671 B1 | 10/2001 | Reesby et al. | |
| 6,298,506 B1 * | 10/2001 | Heinold et al. | 5/613 |
| 6,302,579 B1 | 10/2001 | Meyer | |
| 6,421,553 B1 | 7/2002 | Costa et al. | |
| 6,437,567 B1 | 8/2002 | Schenck et al. | |
| 6,446,286 B1 | 9/2002 | Karmalawy | |
| 6,459,923 B1 | 10/2002 | Plewes et al. | |
| 6,498,489 B1 | 12/2002 | Vij | |
| 6,521,209 B1 | 2/2003 | Meade et al. | |
| 6,526,299 B2 | 2/2003 | Pickard | |
| 6,593,101 B2 | 7/2003 | Richards-Kortum et al. | |
| 6,639,406 B1 | 10/2003 | Boskamp et al. | |
| 6,640,364 B1 | 11/2003 | Josephson | |
| 6,675,037 B1 | 1/2004 | Tsekos | |
| 6,697,652 B2 | 2/2004 | Georgakoudi et al. | |
| 6,723,303 B1 | 4/2004 | Quay | |
| 6,806,711 B2 | 10/2004 | Reykowski | |
| 6,822,450 B2 | 11/2004 | Klinge et al. | |
| 6,867,593 B2 | 3/2005 | Menon et al. | |
| 6,904,305 B2 | 6/2005 | Tsekos | |
| 6,922,859 B2 * | 8/2005 | Gagnon et al. | 5/601 |
| 7,011,447 B2 * | 3/2006 | Moyers | 378/204 |
| 7,023,209 B2 | 4/2006 | Zhang et al. | |
| 7,024,711 B1 * | 4/2006 | Stasney et al. | 5/613 |
| 7,373,676 B2 * | 5/2008 | Markovic et al. | 5/601 |
| 7,379,769 B2 | 5/2008 | Piron et al. | |
| 2001/0011394 A1 * | 8/2001 | Heimbrock et al. | 5/618 |
| 2001/0039378 A1 | 11/2001 | Lampman et al. | |
| 2002/0056161 A1 * | 5/2002 | Falbo et al. | 5/601 |
| 2002/0073717 A1 | 6/2002 | Dean | |
| 2002/0095730 A1 * | 7/2002 | Al-Kassim et al. | 5/601 |
| 2002/0099264 A1 | 7/2002 | Fontenot | |
| 2002/0131551 A1 | 9/2002 | Johnson et al. | |
| 2002/0156365 A1 | 10/2002 | Tsekos | |
| 2002/0164810 A1 | 11/2002 | Dukor et al. | |
| 2002/0180442 A1 | 12/2002 | Vij | |
| 2002/0193815 A1 | 12/2002 | Foerster | |
| 2003/0007598 A1 | 1/2003 | Wang | |
| 2003/0191397 A1 | 10/2003 | Webb et al. | |
| 2003/0194050 A1 | 10/2003 | Eberhard et al. | |
| 2003/0199753 A1 | 10/2003 | Hibner et al. | |
| 2003/0199754 A1 | 10/2003 | Hibner et al. | |
| 2003/0206019 A1 | 11/2003 | Boskamp et al. | |
| 2004/0183534 A1 | 9/2004 | Chan et al. | |
| 2004/0216233 A1 * | 11/2004 | Ludwig et al. | 5/601 |
| 2005/0005356 A1 * | 1/2005 | Zacharopoulos et al. | 5/601 |
| 2005/0059877 A1 * | 3/2005 | Falbo | 600/407 |
| 2005/0104591 A1 | 5/2005 | Qu et al. | |
| 2005/0228267 A1 | 10/2005 | Bulkes et al. | |
| 2006/0026761 A1 * | 2/2006 | Falbo | 5/601 |
| 2006/0133580 A1 | 6/2006 | Vezina | |
| 2007/0039101 A1 * | 2/2007 | Luginbuhl et al. | 5/600 |
| 2007/0050908 A1 * | 3/2007 | Kogan et al. | 5/128 |
| 2007/0161935 A1 * | 7/2007 | Torrie et al. | 602/32 |
| 2007/0238949 A1 * | 10/2007 | Wang et al. | 600/407 |
| 2008/0005839 A1 * | 1/2008 | Kogan et al. | 5/601 |
| 2008/0077005 A1 | 3/2008 | Piron et al. | |

FOREIGN PATENT DOCUMENTS

| | | |
|---|---|---|
| EP | 0753758 | 1/1997 |
| WO | WO 01/28412 | 4/2001 |
| WO | WO 02/39135 | 5/2002 |

OTHER PUBLICATIONS

Gregory Palmer, et al., "Optimal Method for Fluorescence and Diffuse Reflctance Measurements of Tissue Biopsy Samples," Lasers in Surgery and Medicine, 30:191-200 (2002).

Nicole Kline, et al., "Raman Chemical Imaging of Breast Tissue," Journal of Raman Spectroscopy, vol. 28, 119-124 (1997).

Ramasamy Manoharan, et al., "Histochemical Analysis of Biological Tissues using Raman Spectroscopy," Spectrochimica Acta Part A.52 (1996) 215-249.

K.E. Shafer-Peltier, et al., "Raman Microspectroscopic Model of Human Breast Tissue: Implications for Breast Cancer Diagnosis in Vivo," Journal of Raman Spectroscopy, 2002, 33:552-563.

Ntziachrstos V., et al., "Concurrent MRI and Diffuse Optical Tomography of Breast After Indocyanine Green Enhancement," PNAS, Mar. 14,2000, vol. 97, No. 6, 2767-2772.

Buadu LD, Murakami, J, Murayama S., et al., "Breast Lesions: Correlation of Contrast Medium Enhancement Patterns on MR Images with Histophathological Findings and Tumor Angiogenesis," Radiology 1996, 200:639-649.

M. Kriege, C.T.M. Brekelmans, C. Boetes, J. Klijn., et al., "Efficacy of MRI and Mammography for Breast-Cancer Screening in Women with a Familial or Genetic Predisposition," N. Engl J Med 2004; 351:427-437.

Non-Final Office Action mailed Feb. 9, 2007 in U.S. Appl. No. 10/916,738.

Non-Final Office Action mailed Sep. 24, 2007 in U.S. Appl. No. 10/916,738.

Non-Final Office Action mailed Nov. 16, 2009 in U.S. Appl. No. 11/442,944.

Final Office Action mailed Feb. 5, 2010 in U.S. Appl. No. 12/031,271.

Non-Final Office Action mailed May 12, 2009 in U.S. Appl. No. 12/031,271.

International Search Report mailed Dec. 13, 2007 in International Application No. PCT/CA2007/001513.

International Preliminary Report on Patentability issued Mar. 3, 2009 in International Application No. PCT/CA2007/001513.

European Search Report mailed Jul. 30, 2009 in EP Application No. 09007010.3.

European Search Report mailed Oct. 16, 2009 in EP Application No. 09007010.3.

Non-Final Office Action mailed Jan. 22, 2010 in U.S. Appl. No. 11/447,053.

* cited by examiner

SUPINE PATIENT SUPPORT FOR MEDICAL IMAGING

CROSS-REFERENCE TO RELATED APPLICATIONS

This Application claims the benefit of Provisional U.S. Patent Application Ser. No. 60/931,542, filed May 23, 2007, and is a continuation-in-part application of U.S. patent application Ser. No. 11/949,445, filed Dec. 3, 2007, which claims the benefit of Provisional U.S. Patent Application Ser. No. 60/872,345, filed Dec. 1, 2006, and which is in turn a continuation-in-part of U.S. patent application Ser. No. 10/916,738, filed Aug. 12, 2004, issuing as U.S. Pat. No. 7,379,769 on May 27, 2008, which claims the benefit of U.S. Provisional Application Ser. No. 60/506,784, filed Sep. 30, 2003. These prior applications are incorporated herein by reference in their entirety.

FIELD OF THE INVENTION

The invention relates to a patient bed, and more particularly to a patient bed for imaging and/or interventional use with a medical imaging system, especially magnetic resonance imaging systems.

BACKGROUND OF THE INVENTION

The present disclosure relates generally to a method and apparatus for imaging selected regions of a patient, especially the lower torso, pelvis and lower body of a supine patient, such as during gynecological and prostate imaging, such as for detecting the presence of malignancies in this region, such as penile cancer, testicular cancer, cervical cancer, pelvic cancer and the like, and particularly to the mechanical apparatus which makes access to the lower torso and lower body possible.

Magnetic resonance imaging (MRI) is useful in assessing the presence, size and location of diseased or damaged tissues in the lower body, such as a prostate tumor, for surgical planning, and for guiding therapeutic and diagnostic procedures such as biopsy, brachytherapy and staging of disease. In addition to conventional T1 and T2-weighted MR imaging, MR spectroscopy has also proven very useful in assessing metabolic activity in diseased tissue. The use of computed tomography imaging (CT) and positron emission tomography (PET) and C-arm x-ray are also well known in the medical field for similar imaging objectives. During imaging procedures, it is necessary for the patient to lie motionless for an extended period of time, in some cases even holding their breath. Longer imaging protocols make breath holding impracticable, and so the respiratory motion may degrade the images even in a patient who lies motionless. Lying immobile for extended periods in some positions poses hazards to the patient's health, whether or not they are sedated.

When it is desired to introduce a probe or interventional medical device to tissues, it is often necessary to remove the patient from the imager's imaging volume. This is the case for various designs of MRI, PET, CT and when C-arm X-ray is used—either the patient is removed from the imaging volume, or the imager is moved away from the patient tissues. In such cases, it is important that the physical arrangement of the patient's tissues is not altered between the imaging position and the intervention position. This is not a procedure that is easily controlled because of random movements and uncontrollable anomalies. These factors can affect the quality and even the reliability of results.

Imaging and intervention near the pelvis in particular often requires devices to be introduced into tissues via the rectum, genitals or perineum. Typical patient beds used for imaging have shapes which limit access to patient tissues and do not provide an easy means of attachment for the specialized devices used in image-guided intervention. Thus there is a need for a patient bed for use with medical imaging equipment which provides access and line-of-sight to the underside of the lower body and a means of positioning specialized devices for imaging and intervention.

SUMMARY OF THE INVENTION

The present invention provides a patient support for use with medical imaging and/or intervention. Generally, the patient support can have a tabletop and a stretcher, where the patient is supported by the tabletop and the tabletop can be supported by the stretcher.

Specifically, one aspect of the invention provides a patient supporting apparatus for imaging and intervention with a medical imaging system. The tabletop has a superior end coupled to an inferior end by a bridge member. The bridge member has a lesser width than that of the superior and inferior ends of the tabletop so as to define an open area. The stretcher also has a superior end coupled to an inferior end by a bridge member with a lesser width than that of the stretcher ends so as to define an open area. The stretcher is configured to support the tabletop such that in at least one position the open areas of the tabletop and the stretcher are in registration.

Another aspect of the invention provides a medical imaging system including such a tabletop and stretcher arrangement. Further, an imager is provided for acquiring data used to generate a multi-dimensional image of an area of interest of a patient. The imager having an access opening in communication with an imaging volume, and the stretcher is configured to transport the tabletop through the access opening and into the imaging volume of the imager.

In some cases it is advantageous to position the patient on their back (supine) to reduce risk to the patient, minimize tissue motion or for improved access to the area of interest. One such example of a procedure used with supine patient positioning relates to prostate imaging and intervention, where MR imaging coils and/or biopsy guidance probes may be inserted in the rectum for these procedures. Use of transrectal devices traditionally precludes supine patient positioning.

In accordance with the present invention, the tabletop and stretcher are specially made to provide physical access to the patient's lower body (including genitals, rectum, legs and pelvis). Additionally, features may be provided in the tabletop and stretcher system which allow the positioning and fixation of such devices as may be used in intervention and imaging procedures such as lights, fluid catchments, biopsy needles, biopsy needle guides, patient positioning restraints, pads and/or guides, MR imaging coils, means of routing cables and electronics, visual alignment marks, fiducial markers, ventilation, patient transfer devices and so forth. The fixation member can be coupled to the tabletop to secure a medical device to the tabletop. In particular, it can mount a guidance plate having an array of openings for receiving the medical device. And further, it can mount first and second guidance plates each having an array of openings. At least one of the guidance plate can be moved by an actuator to displace the openings of the first guidance plate with respect to the openings of the second guidance plate, thereby permitting the plates to clamp the device in place.

The portion of the tabletop of the present invention corresponding to the portion supporting the lower body has an open field of view such as a gap or a narrowing which affords clearance for the physician's line-of-sight, provides access and permits clearance of devices used in the imaging or interventional procedure. Preferably, the open area of the tabletop is located inferior of a mid-line extending in the width dimension and bisecting the tabletop between the superior and inferior ends of the tabletop so as to provide access to a pelvic region of the patent. When the patient's tissues are away from the imaging volume, the tabletop's narrowing or gap aligns with a corresponding gap or narrowing in the stretcher which supports the tabletop so that access to tissues is maximized.

The width of the bridge members of the tabletop and stretcher are designed to be of significantly lesser width than that of the superior and inferior ends, such that a wide gap or open area are provide for access and clear line-of-site. For example, the bridge member for each of the tabletop and stretcher is less than half the width of one of the superior and inferior ends, preferably even less than that, and of a significant length, such as at least 0.3 meters. Also, the bridge members can extend along an axis offset from the long centerline extending between the ends so as not to interfere with viewing or placing instruments at the patient's line of symmetry.

Each bridge section can be one or more members that are permanently attached between the ends, or they can be movable or removable relative thereto. The bridges can be straight sections lying in the plane of the ends or straight or actuate surfaces extending outside of the plane of one or more of the ends, such as being arcuate in a plane perpendicular to a plane defining an end. A bridge can extend only both sides so that the opening formed is bounded on all sides, or it can be open at one or more sides.

The stretcher provided according to the present technology is constructed using imaging-compatible materials and provides an opening, gap or narrowing which corresponds to the gap or narrowing of the tabletop when the tabletop is resting on the stretcher. The stretcher may be used in place of the imager's general-purpose patient support stretcher in cases where the general purpose stretcher is a removable type, or the stretcher of the present invention may provide clearance for a non-removable imager's stretcher or stage.

According to another aspect of the present invention, the apparatus can include patient immobilizing attachments coupled to the tabletop. For example, the tabletop provides a means for supporting the patient's lower legs such that the patient remains supported in a stable position whether inside or outside the imaging volume. It may also be advantageous to extend the tabletop's patient supporting surface temporarily into the tabletop's gap or narrowing during initial set up and positioning of the patient using removable panels or the like, however, the gap or narrowing is open or opened for positioning of devices used in imaging and intervention. A head rest, and straps or belts for immobilizing the torso, arms or other body parts may also be attached to the tabletop or stretcher to further stabilize the patient.

According to another aspect of the present invention, there is a method for providing access to a patient's pelvis and lower body by bringing the tabletop and stretcher components of a patient carriage system to the imaging system and aligning the carriage system and components such that the tabletop may be conveyed into the imaging volume. To facilitate this, the tabletop can be coupled to the stretcher so as to permit movement of the tabletop relative the stretcher or a support base to which the stretcher is fixedly or movable mounted.

The tissue of interest is exposed to view and access by the operator within the gap or narrowing of the tabletop, and the imaging procedure is performed, including the delivery of any imaging and interventional devices to the patient tissues.

Specifically, the inventive method provides for supporting a patient in a supine position when acquiring a medical image of the patient's pelvic region using an imager having an imaging volume. This method includes providing a tabletop and a stretcher as defined above. Both components define open areas between their superior and inferior ends, preferably inferior of mid-lines bisecting tabletop and stretcher between their ends. The tabletop supports the stretcher such that in at least one position the open areas of the tabletop and the stretcher are in registration. The tabletop supports the patient in a supine position with the patient's head at the superior end, the patient's feet at the inferior end and the patient's pelvic region in proximity to the open area. The tabletop is transported into the imaging volume of the imager so that the imager can acquire an image of the patient's pelvic region.

DETAILED DESCRIPTION OF THE EXEMPLARY EMBODIMENT(S)

Figure 6:
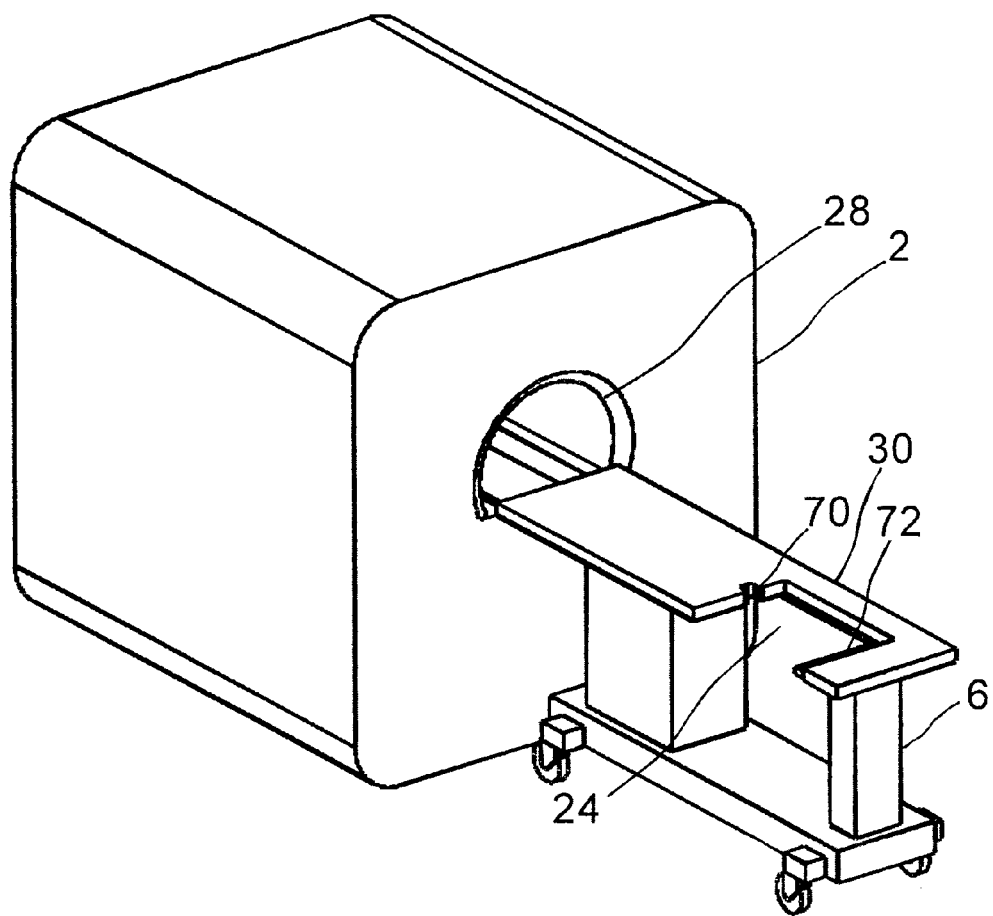
FIG. 6 is a perspective illustration of a tabletop on another exemplary embodiment of a stretcher which can be used in place of an imager's removable stretcher.
Figure 7:
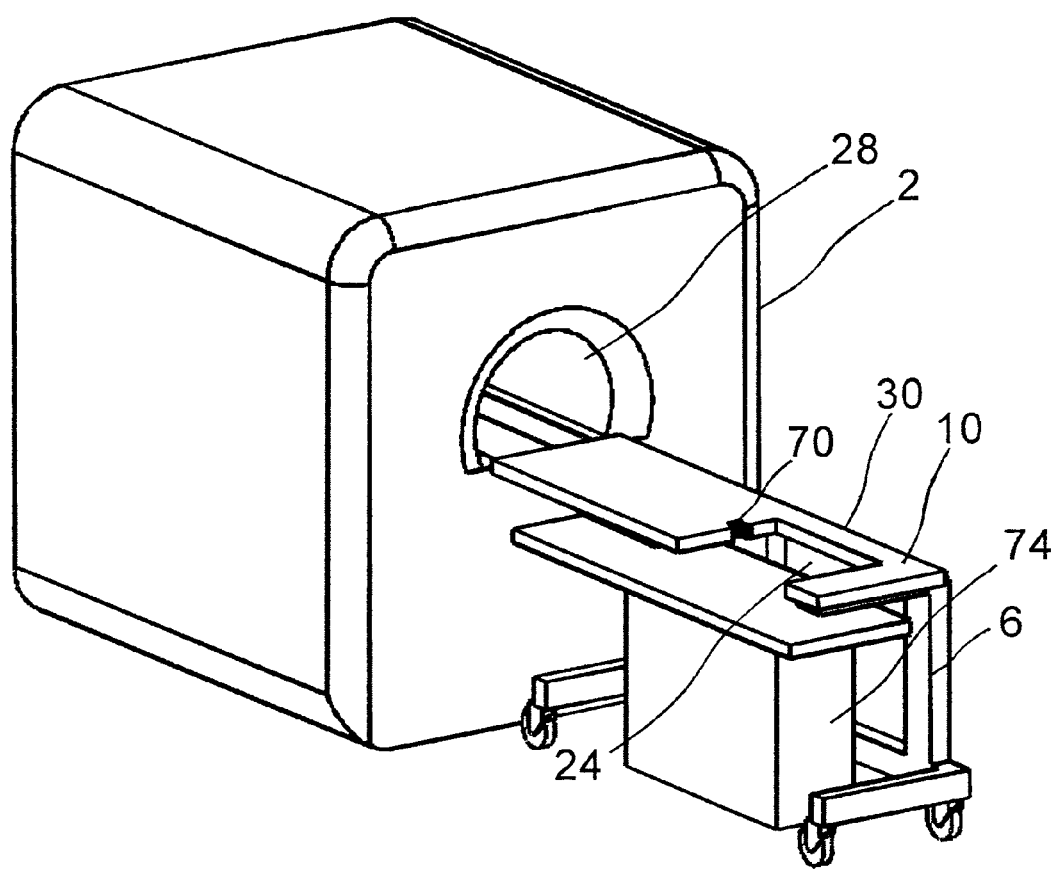
FIG. 7 is a perspective illustration of a tabletop on an exemplary embodiment of a stretcher which can be used in the presence of an imager's non-removable stage.
Figure 8:
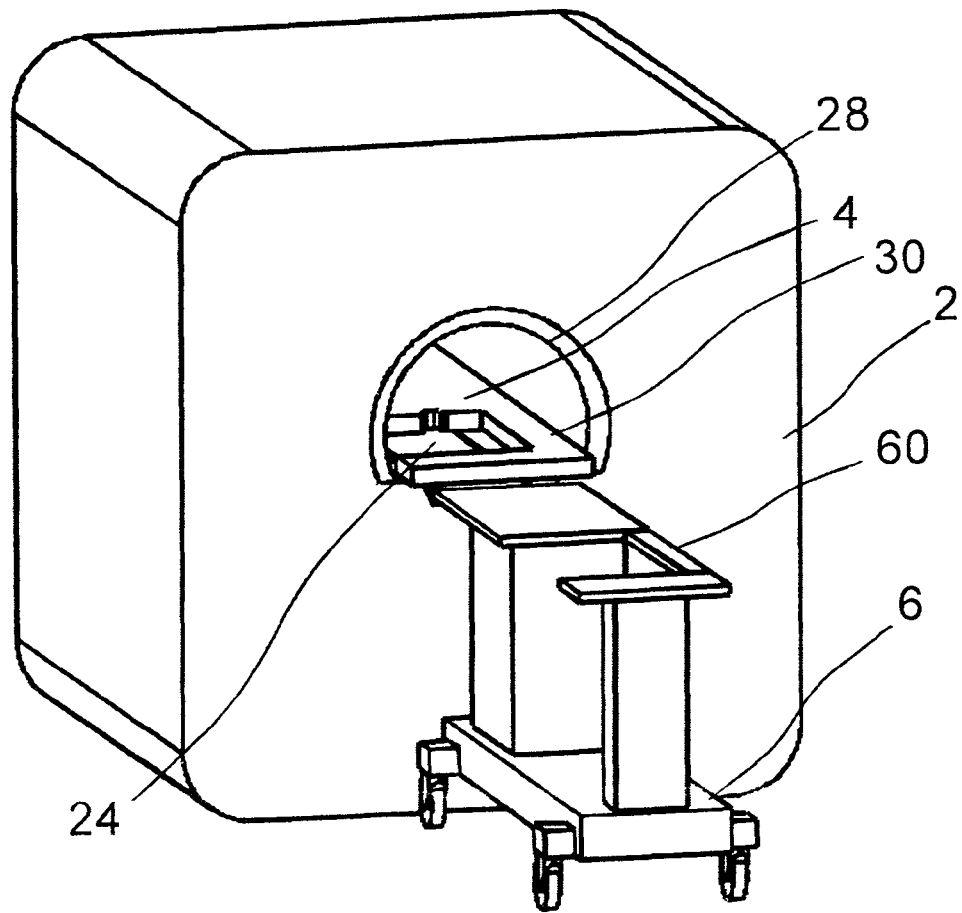
FIG. 8 is a side view of a tabletop (patient not shown) which has been advanced to the imaging position.

A medical imaging system or imager 2, such as shown in FIGS. 6-8, has an aperture, opening, window or other accessible volume or area 28 which in turn contains or leads into an imaging volume 4 into which a patient is moved during an imaging procedure. The data acquired by the imager 2 is used to create a two- or three-dimensional image of the organ or area of interest of the patient being examined. In accordance with the present invention, a movable stretcher 6 which may have an elevating portion is used initially to support a tabletop 10 which in turn supports a supine patient who may eventually be advanced, along with the tabletop 10 into the imaging volume 4.

Figure 4:
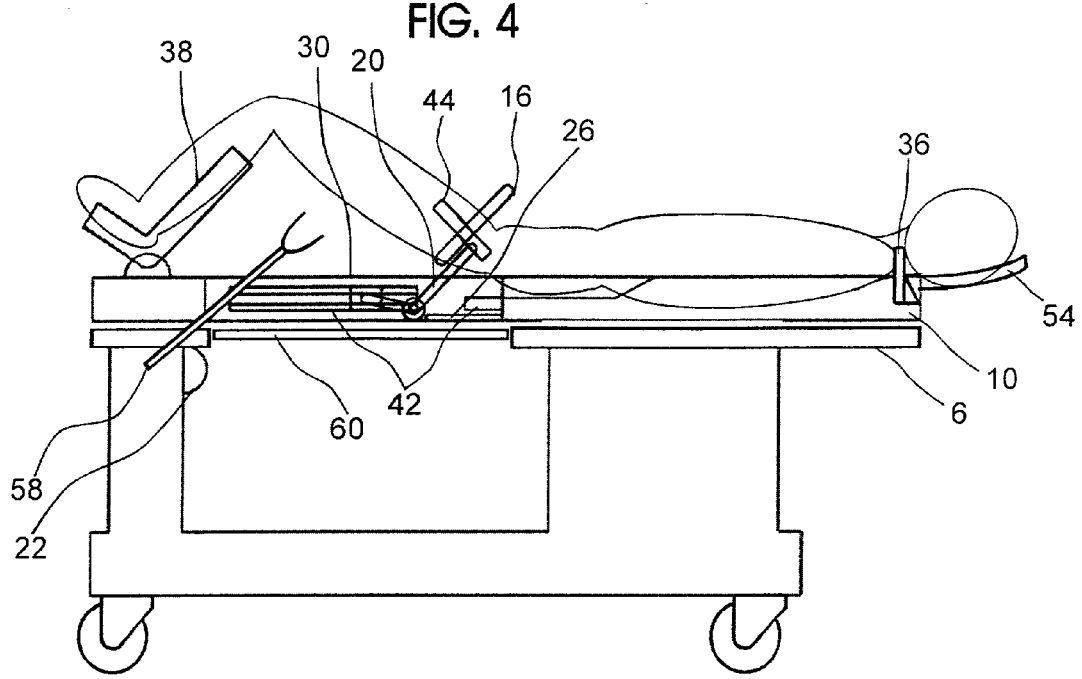
FIG. 4 depicts various attachments to the tabletop and stretcher which are enabled by the gap or narrowing of the tabletop and stretcher. A guidance plate is shown which has not been positioned near the rectum or perineum.
Figure 5:
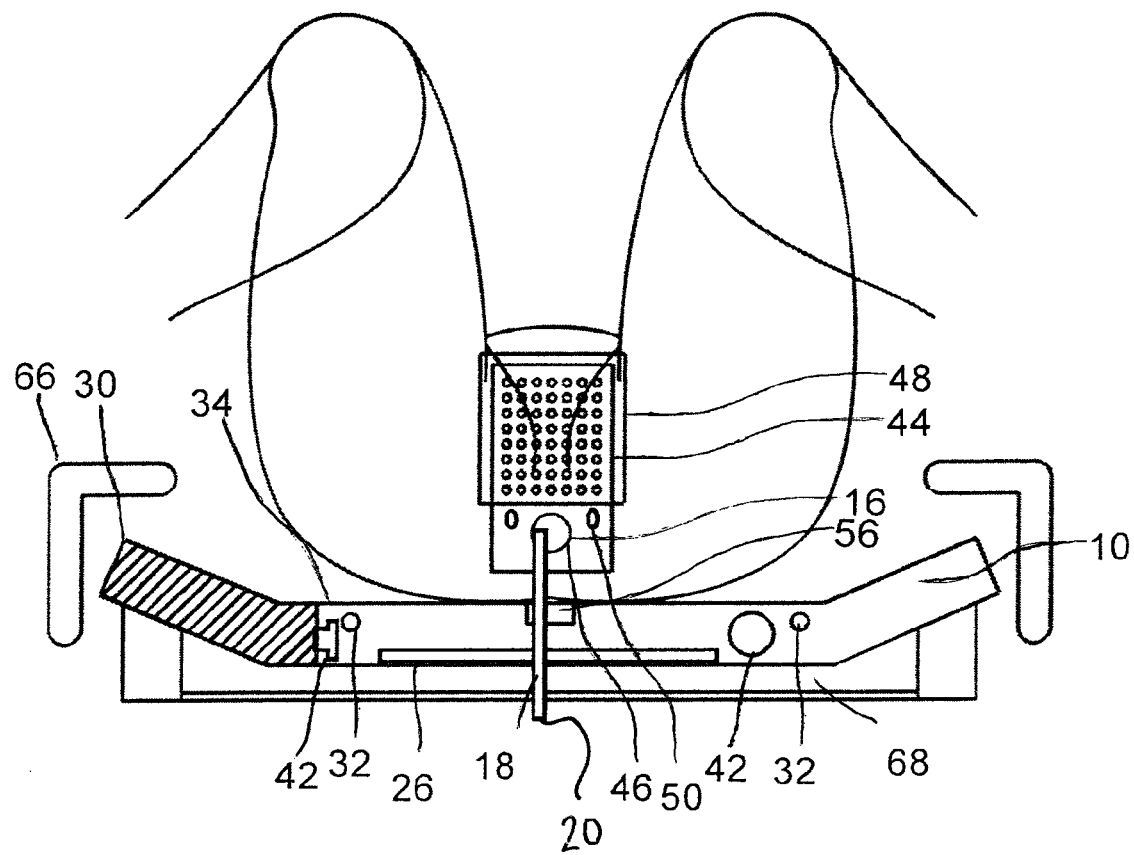
FIG. 5 is a sectional front view of a tabletop and stretcher depicting various attachments enabled by the gap or narrowing of the tabletop and stretcher. A guidance plate is shown which has been positioned near the rectum and perineum.

During an imaging or interventional procedure, a physician, technician or other operator of the imaging device may position a number of devices inside the tissues which are under examination. This may include biopsy needles, biopsy needle guides 16 and trans-rectal MR imaging coils 18, as shown in FIGS. 4 and 5. Because of the limited size of the imaging volumes 4 and associated apertures 28 of imaging devices, these devices are preferentially positioned when the patient is away from the imaging volume 4, with the tabletop 10 on the stretcher 6. The positioning of these devices may rely on the acquired images for guidance and it is important that the patient not move any body parts during the procedure. Therefore, it must be possible to displace the patient to and from the imaging volume 4 without disturbing the relative position of the anatomy, which is often caused by shifting the body position of the patient relative to the tabletop. This movement can be reduced and nearly eliminated by having the patient and tabletop physical relationship relatively fixed, directing medical instrumentation to the patient while in that fixed relationship, and then moving the tabletop and patient relative to the stretcher and relative to the imaging system.

Figure 1:
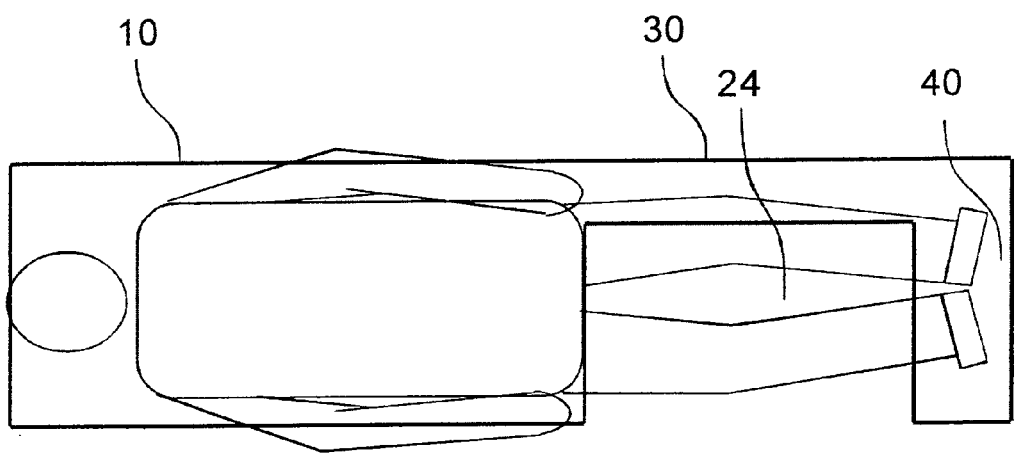
FIG. 1 is a top view of an exemplary embodiment of a tabletop having a gap or narrowing configured to provide access to the lower torso and lower body of a supine patient.
Figure 2:
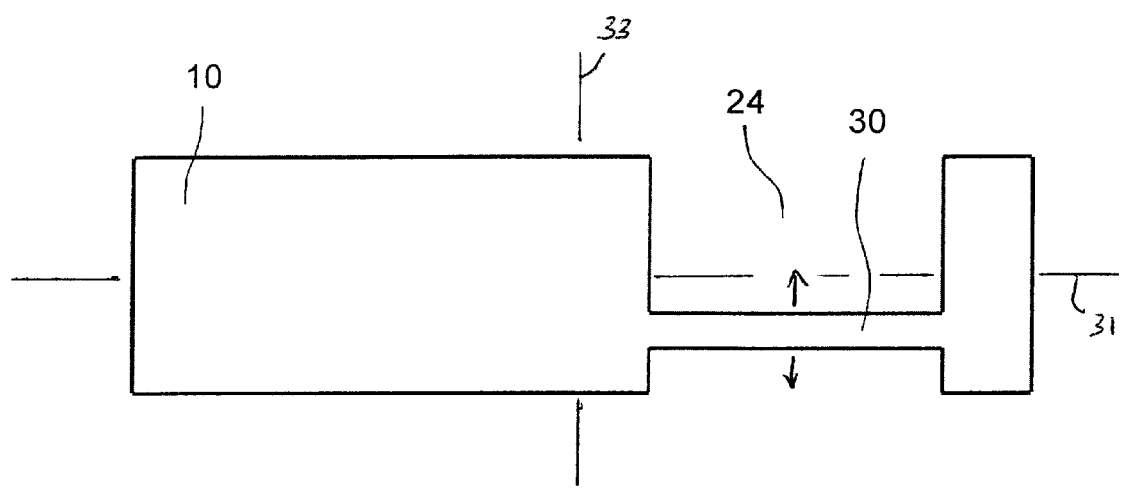
FIG. 2 is a top view of an additional exemplary embodiment of a tabletop having a gap or narrowing configured to provide access to the lower torso and lower body of a supine patient.
Figure 3:
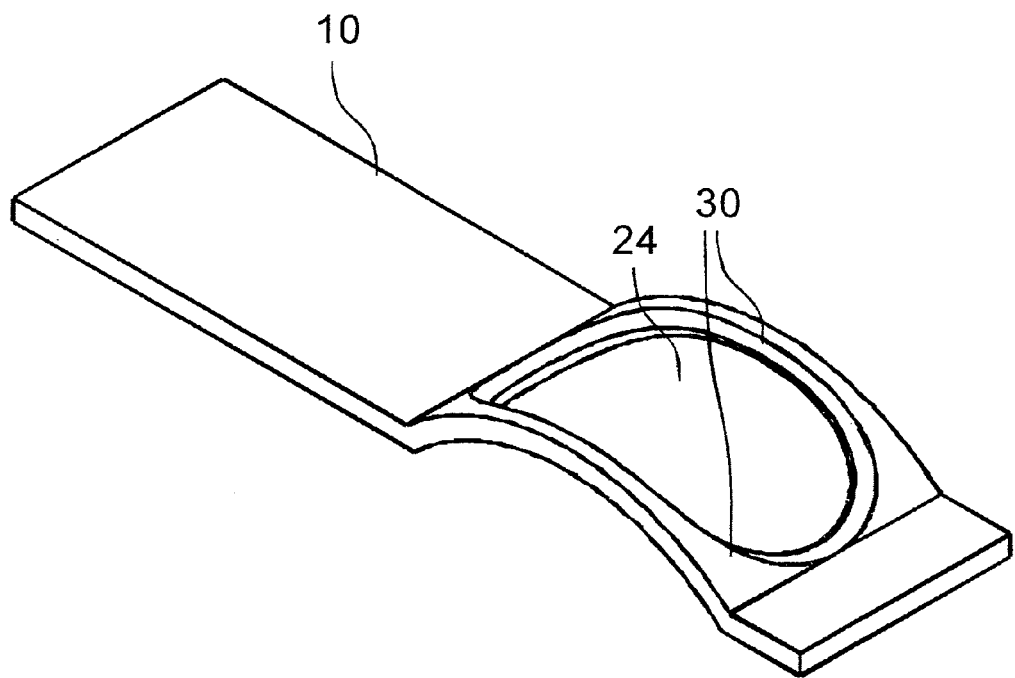
FIG. 3 is a top perspective view of an additional exemplary embodiment of a tabletop having a gap or narrowing configured to provide access to the lower torso and lower body of a supine patient. The members connecting the upper and lower body sections of the tabletop prevent the patient's legs from touching the aperture of the imager.

Furthermore, it is sometimes advantageous to place the patient in a supine position for imaging and/or intervention. Also, it is sometimes desirable or necessary to introduce imaging and interventional devices into a supine patient such as trans-rectal MR imaging coils 18, biopsy needles, intra-uterus insertions, brachytherapy seeds or biopsy needle guides 16 via the rectum or perineum. These are delivered from between the patient's legs or from beneath (posterior to) the patient. In this case, as shown in FIGS. 1-3, a gap, channel, depression or narrowing 24 of the tabletop is needed below the general plane of a supporting surface for the patient to provide access for the device, for the physician's hand and arm and to provide the physician line-of-sight to the tissue. The gap or narrowing affords maximum space for a physician to get close to the patient tissues, while still maintaining effective supporting continuity of the tabletop from head to foot so that the feet, legs, hips and the like may be supported immobile relative to the upper body. It is advantageous that any structural, bridging or supporting members or surfaces 30 connecting the superior and inferior parts of the tabletop do not pass through the centre plane of the tabletop since this is the patient's plane of symmetry, shown in FIG. 2 as centerline 31, and space in this area may be needed for imaging, access by medical personnel and interventional devices.

In a further embodiment of the present invention, it is made possible to extend the patient on the tabletop 10, which tabletop is substantially radiolucent (that is, penetrable by at least desired wavelengths and formats of electromagnetic imaging radiation, magnetic radiation, and X-rays) further towards the foot (inferior) end of the tabletop so that the patient's pelvis overhangs the stretcher in order that a C-arm x-ray may be used to image the area of interest (such as the prostate, colon, penis, testicles, cervix, etc) without undue distortion or attenuation of the imaging radiation or field. An embodiment of the present invention additionally provides a visible line or hash mark on the tabletop 10 indicating the approximate position of the region of interest in the pelvis (such as the prostate), which hash mark or line is used for patient preparation before advancing to the imaging volume. These may also be adjustable slides or indicators that can be adjusted for individual patients.

The biopsy needles, biopsy needle guides 16, brachytherapy delivery needles 64 and other interventional devices may integrate an optical or electromagnetic position tracking sensor. The position data acquired from such sensors may be co-registered with the medical imaging data in order to verify the real-time position of the tracked interventional devices. The gap or narrowing 24 in the tabletop need not have a regular or rectangular shape. For example, geometric and patterned shapes such as a curved edge, conical shape, oval shape 70 and the like under the patient's buttocks afford maximum support for the pelvic girdle while allowing maximum access to the rectum and perineum.

One general description of this technology may be presented as a patient supporting apparatus having a tabletop and a stretcher. The tabletop may be displaced into the imager where tabletop has a gap or open area. In the case where the region of interest is the pelvic region, the open area or gap for each of the tabletop and the stretcher are located at an inferior side of a mid-line (33 in FIG. 2) that extends in the width dimension and bisects the tabletop and stretcher lengthwise, that is between superior and inferior ends. The gaps should be sufficiently wide and long as to enable access to patient regions of interest. For example, the gap should extend for a distance that is at least 25%, preferably at least 35% and more preferably more than half the left-right width of the tabletop. The gap may be permanent in the tabletop, or a filling structure may be removed (e.g., inferior to the patient's pelvis) within a region of at least 0.3 m in length, preferably at least 0.7 m in length. The stretcher supports the tabletop and includes a gap or narrowing, preferably of equal or greater size than the tabletop's gap, so that the access of the operator's hand, arm, and line of sight is not obstructed from the gap or narrowing of the tabletop.

Additional embodiments include a tabletop 10 which has a hollow or open section or conduit which permits cables to be routed underneath the tabletop's patient supporting surface. In an alternate embodiment, cables are routed underneath the patient supporting surface 34 without causing danger or discomfort by routing cables in a trough 56, tunnel 68, pipe or groove in the tabletop's surface (see FIG. 5). It is advantageous to integrate clips or a wire mould for running lines for imaging devices, pulse-oximeter cables, IV tubes, etc. along the length of the tabletop.

In one embodiment, the tabletop 10 integrates an extension 54 at the head (superior) end which overhangs the superior-inferior extent of the stretcher 6 (see FIG. 6). This is an integrated, yet separately adjustable support for the head and may extend direct support to the neck. This extension 54 may be adjustable and removable to suit the patient size and the positioning desired. In some MR imagers, this permits the use of shorter coil cables. In an alternate embodiment, the tabletop 10 can be used with a general purpose imaging stretcher, and may be rolled on wheels so that the patient's lower body overhands the inferior edge of said general purpose stretcher, thereby creating interventional access to the tissues of the lower torso.

In accordance with the invention, it is advantageous to provide a means (such as an arm 20) of positioning and fixing (securing the device(s) relative to a point on the tabletop) an imaging or interventional device or devices in proximity to the patient's tissues. This fixation means is affixed (permanently or removeably) to the tabletop 10 at one end and may be locked in position. In one embodiment, as shown in FIG. 4, the adjustable arm 20 may be mounted to a superior-inferior slider 42. In another embodiment, the arm 20 or may integrate two or more rotating or pivoting or otherwise 2- or 3-dimensionally adjustable joints. In any case, the arm should be lockable with one or two controls, each of which can be locked with a single hand. Snaps, toggles, levered closures, plug and hole engagement and even fabric locks (e.g., Velcro® fasteners) may be used. In this way, the arm can be held in place with one hand and locked in place with the other. Since the structural arm 20 travels with the patient to the imaging volume 4, it should be made of materials which will not interfere with the imaging such as copper alloys, engineering polymers or the like. Such a structural arm 20 should be removable, so that the system may be used for imaging procedures without being encumbered by unused equipment. In an additional embodiment, the positioning and fixing means (such as an arm 20) may be affixed either to the left or right of the patient's midplane so that the system may be reconfigurably used from either the right or left hand sides.

In accordance with the present invention, the tabletop 10 may be constructed as one piece, or may have a gap or narrowing 24 whose size and location can be modified by displacing bridge members or surfaces 30 connecting superior and inferior parts of the tabletop. These bridge members or surfaces may be one or several, and at least some may be removable entirely. For example, there may be a single bridge member 30 permanent fixed at either the left or right side of the tabletop, as shown in FIG. 1. Or, left and/or right hand bridge members may be removed to improve access from one side, while maintaining continuity of the tabletop 10 from head to foot. In one embodiment, the member 30 may be slid from left to right, over the tabletop or even under the tabletop, as in guide grooves. In another embodiment, the lower body section of the tabletop 10 which integrates the member 30 may be reversed. The double arrows in FIG. 2 represent that the bridge may be adjusted in position relative to the ends and/or removed entirely. While not shown, the same type of arrangement can be provided for any of the other embodiments illustrated in the drawings, for both the tabletop and the stretcher. In another embodiment, the tabletop integrates two gaps or narrowings 24, one of which is filled with a removable pad or panel. The tabletop may then be reversed from head to foot when it is desired to use the aperture, and the pad or panel is moved to the other gap or narrowing 24. This panel may be a sliding insert which slides to cover one or the other of the gaps and preferably may be locked into position so that it does not translate during use. It is not necessary to reverse the tabletop 10 from head to foot if it is possible to use the stretcher 6 with either edge against the imager 2.

In another alternate embodiment of the invention, there is no permanent member 30 which connects the inferior (lower portion supporting the legs and feet) and superior sections (e.g., supporting the upper torso, neck and head) of the tabletop 10. The two sections are bridged prior to advancing the tabletop 10 to the imaging volume 4 by a removeable structural member which can double as the fluid catchment means 26.

The stretcher in the present invention provides an opening, gap or narrowing which corresponds to the gap or narrowing of the tabletop when the tabletop is resting on the stretcher. The stretcher may be used in place of the imager's general-purpose patient support stretcher in embodiments where the general purpose stretcher is a removable type (see FIG. 3). In an alternate embodiment, the stretcher provides clearance for a non-removable imager's stretcher or stage 74 (see FIG. 2).

Figure 9:
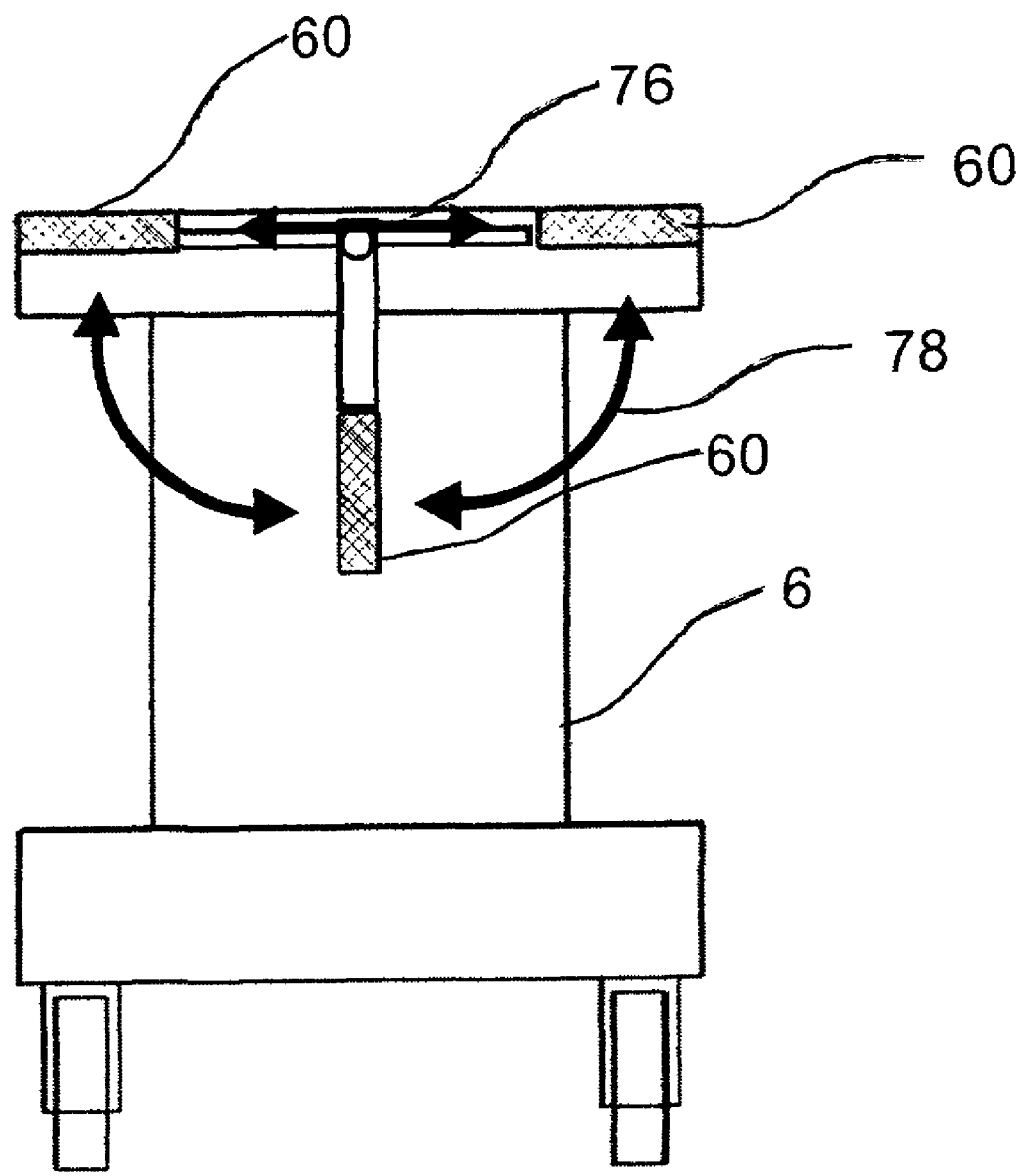
FIG. 9 is a sectional front view of a stretcher depicting two different means for moving the stretcher's bridge from one side to the other, by sliding left-right, or by swinging through an intermediate downward hanging position which provides maximum clearance for the operator.

In one embodiment, the tabletop rolls into the imager's aperture 28 on wheels. The stretcher may provide a continuous upper surface which continuously supports the rolling tabletop, or the tabletop may be constructed with sufficient stiffness and strength that it can roll over a discontinuous tabletop surface while supporting a patient's load. Additionally, in an alternate embodiment, the stretcher may have a bridge 60 in its top surface which supports a rolling tabletop when traversing the stretcher into the imager's aperture 28, but which may later be removed, slid away or folded away exposing a large gap in the stretcher to maximize access to patient tissues. In a further alternative embodiment, as shown in FIG. 9, the stretcher's bridge 60 may be hinged, foldable, accordion foldable and/or slidably mounted so that it can be displaced in a left and right direction 76 from one side of the stretcher to the other, or dropped in a swinging direction 78 out of the way of interventional devices. For example, the bridge may slide along glides while collapsing in accordion format, and then be rotated (while still attached to the stretcher) to be folded into a storage section built into the stretcher.

Figure 10:
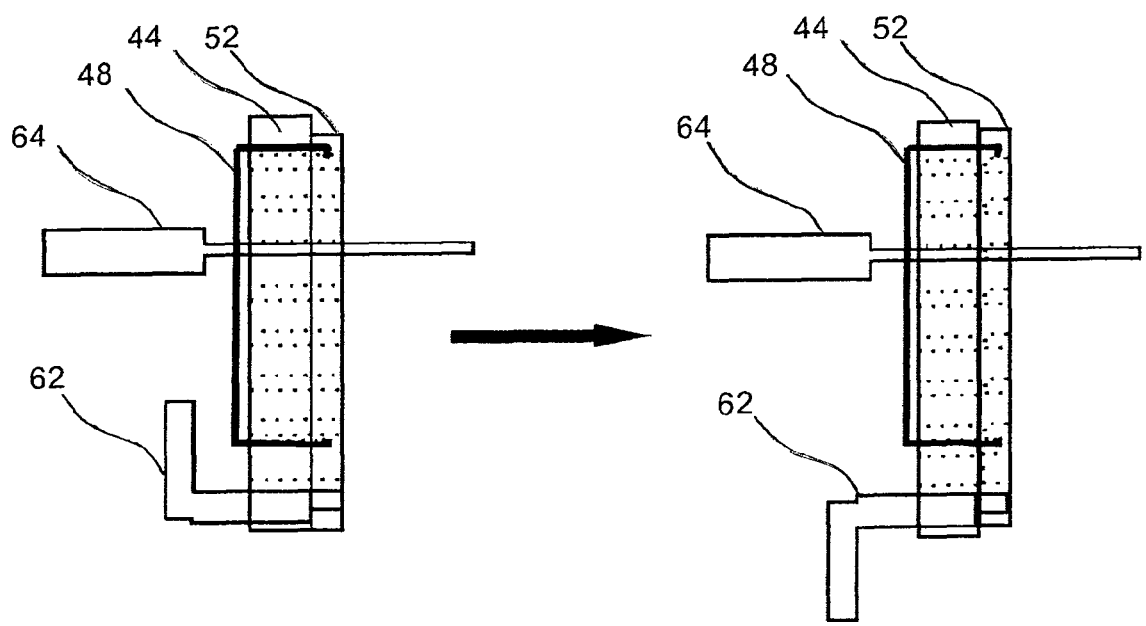
FIG. 10 is a side view of first and second guidance plates having arrays of holes to accept interventional devices which plates may be displaced using a cam or similar means to offset the holes slightly in order to lock the interventional devices in place.

In accordance with the present invention, it is made possible to position a guidance plate 44 against the perineum which plate has an array of holes which are sized to accept one or more needles 64 which can be a biopsy or a brachytherapy seeding needle. As shown in FIGS. 4 and 5, the guidance plate 44 can be used to position other devices such as a trans-rectal biopsy needle guide 16 through an aperture 46. The guidance plate 44 can accept an MR imaging coil 48, which coil may have a half-saddle coil design or Helmholtz design which provides optimal imaging of the plate and any fiducial markers 50 in or on the plate so that the location of the array of holes in the plate 44 relative to tissue may be discovered. The guidance plate 44 is advantageously constructed from materials which are largely invisible and at least non-distorting to the imaging modality being used. It is then possible to visualize the holes in the plate by adding a substance to those holes which is visible to the imaging modality (e.g. water-based gel under MR imaging). As shown in FIG. 10, it is possible to lock the needles 64 inserted through guidance plate 44 and a second guidance plate 52 having a similar array of holes in position using by a cam 62, step motor, threaded engagement, step engagement, or other quantified movement control which slightly displaces the second guidance plate. The action of displacing the second biopsy plate 52 will clamp the needles 64 in place between the two plates preventing the needles from moving. Another embodiment of the grid integrates a means of illumination into the grid such as an LED, or a glowing or bioluminescent pigment.

When, in accordance with the present invention, access is provided to the rectum and perineum, it is advantageous to provide a means of illumination for that area to help the physician visualize and position devices. The lighting means 22, such as shown in FIG. 4, is preferably a low voltage, low wattage (<15 Volt, <15 Watt) lamp or lamps affixed to the stretcher 6 and shining onto the patient's lower torso, rectum and perineum from an inferior/posterior direction. However, it is also possible to use higher voltage and power, and to affix the lighting means to the tabletop 10 or arm 20. It is also desirable that the angle, orientation, elevation and sideways displacement of the lighting element be adjustable and that there is easy access to bulbs for replacement. Interchangeable light elements, that is a snap in socket arrangement on the tabletop-stretcher system facilitates rapid exchange of the lighting elements and allows for different shapes, intensities and colors to be replaced rapidly in advance of or during procedures. It is desirable that it be possible to automatically extinguish the lights 22 when the tabletop 10 is advanced into the imager's aperture 28. In another embodiment, the lighting housing 22 integrates both a lamp and a battery in order that wires carrying power to the lamps need not be routed through the stretcher or tabletop, and instead these wires are confined to the lighting housing 22.

In the case where a biopsy, prostate seeding or urological procedure (such as a urodynamic test) is to be performed, and there is a possibility of fluids being present in the gap or narrowing 24 of the tabletop 10, it is advantageous to provide a fluid catchment means 26, as shown in FIG. 5, such as a simple tray, to the tabletop which travels with the patient and tabletop to and from the imaging volume 4. Such a catchment means 26 can be removed for access to the area of interest and for cleaning, and may be of a simple, thin construction, such as a plastic tray with or without a rim, drain and/or fluid collection reservoir. It is also desirable to have a reduced pressure system available in the fluid catchment system, which can be simply a tube with a vacuum pressure at a distal end. The tube may be provided of a material that will not adversely impact the imaging means. For long duration imaging procedures and procedures where large liquid intake may have been required, this can be very desirable.

An aperture 28 of an imager 2 is usually a restricted space (restricted in shape, dimensions, volume and materials allowed) and often other devices such as MR imaging coils 32 must be positioned on top of (anterior to) the patient's stomach and pelvis, and underneath (posterior to) their waist and buttocks. It is therefore advantageous to keep the tabletop 10 thin in the anterior-posterior direction, particularly in the region under the patient's waist and pelvis. On the other hand, raising the patient's pelvis up towards the central axis of the imager can produce improved images (as in the case of MRI), provided there is room in the imager's aperture 28 and this can require greater strength in the tabletop, particularly in various sections thereof. In one possible embodiment patient space is maximized by integrating an MR imaging coil 32 into the tabletop, or by placing it directly underneath the patient supporting surface 34. In another embodiment, space is maximized by creating a cutout the same size and shape as the MR imaging coil 32 (or the coil plus a modular enclosure) in the patient supporting surface 34. In either case, in accordance with the present invention it is possible to lower or raise the patient's pelvis by using various thicknesses of pads and/or spacers under the patient's pelvis to raise the tissue of interest as close as possible to the region of optimum imaging (near the aperture's 28 central axis in the case of MRI) while ensuring there is adequate room provided in the anterior direction for the patient and all other equipment.

Immobilization of the patient is important when performing imaging and intervention procedures in this area. For this reason, one embodiment of this invention provides a means of restraining portions of the anatomy that are to be a target of the imaging procedure, such as the pelvis, in anterior-posterior, left-right and superior-inferior directions. This restraining system may, by way of non-limiting examples, comprise a strap or straps which hold the pelvis down against the tabletop's patient supporting surface, molded surface structure that is form fit to general patient dimensions (with or without additional restraining elements) such as evacuated bead-filled bags and snaps such as anklets or bracelets that engage the legs, thighs hips and the like of the patient.

In one embodiment, a lower body flex coil is integrated with the restrains for the pelvis so that when the patient is restrained, the restraint itself carries at least some responsive MRI coil structure into the image-targeted area. Additional embodiments also provide shoulder restraints 36 (see FIG. 4) which prevent the patient from moving in the superior direction by pushing with his feet. This may again take the form of straps looping over the shoulders, similar to those found on a backpack, molded shape restraints, snap locks, or of padded members which may be adjusted in the superior inferior direction, and fixed in position resting on the shoulders (refer to FIG. 4). An alternate embodiment of the present invention includes an alarm which signals the physician that the patient has moved or that the patient has pushed against the leg supports with a force above or approaching a pre-determined threshold.

In one embodiment of the present invention, the tabletop is furnished with supports to keep the arms in at the patient's sides, preventing them from touching the inside of the imager's aperture 28 and extending into targeted image regions on the patient. Similarly, as shown in FIG. 3, the tabletop can provide two members 30 which link the tabletop's superior and inferior sections, which two members 30 prevent the patient's thighs, knees and lower legs from touching the imager's aperture 28. In another embodiment of the present invention, there are handles 66 provided on the tabletop 10 or on the stretcher 6 to the left and right of the patient's waist which the patient can use to help himself slide superior-inferior and left-right when getting positioned prior to the start of the imaging procedure. In a further embodiment it may desired to provide removable or retractable panels to cover the gap or narrowing 24 of the tabletop 10 which panels may support some of the patient's weight while getting positioned, but which may be moved out of the way for the imaging or interventional procedure.

According to the present invention, the legs are supported by adjustable and lockable leg supports 38. As shown in FIG. 4, the legs can be supported by adjustable (longitudinally, horizontally and rotationally) stirrups which affix to the tabletop 10 and hold the feet and lower leg. In another embodiment, there is a broader foot section of the tabletop 40, inferior to the gap or narrowing 24 which holds the leg supports 38 and which is in turn supported by the stretcher 6. In the preferred embodiment of the leg support 38, it is possible to keep the left and right foot at the same height, and to support some of the weight of a bent leg on the sole of the foot to combat deep vein thrombosis. In the preferred embodiment of the leg support 38, it is also possible to adjust the position of the leg supports in the superior-inferior position. In additional embodiments of the leg support 38, it is possible to adjust the left-right distance between the feet and to adjust the toe-in/toe-out of the foot. The leg supports preferentially guide at least half of the length of the lower leg so that the knee's position is comfortably constrained and may provide straps or the like to restrain the feet. It should be possible to lock any of the adjustments of the leg support 38 using one hand with a cam, a threaded knob, a lever or the like, so that the operator's other hand may be used to support the leg. In a further embodiment of the invention, the stretcher integrates footrests 72 (see FIG. 6) for resting the patient's foot or feet while the leg supports 38 are being prepared and adjusted. An exemplary embodiment of the stretcher's footrest is a simple shelf 72 under the inferior section of the tabletop 40.

As shown in FIG. 4, supports, straps or stirrups 58 can be provided to hold the patients feet or legs in order to bring the patient's knees towards his chest, forming acute angles at the hip and knee joints. These stirrups or straps 58 are only used away from the imaging volume 4 when inserting a trans-rectal imaging coil 18. In one embodiment these features are integrated into the tabletop, and in another they are affixed to the stretcher and may be folded away into the stretcher when not in use.

The gap in the tabletop may correspond with and overlay a gap in the stretcher so that when the two components are properly configured, an opening through both components exist, and when the tabletop is slid away from this particular configuration, an opening is still available through only the tabletop, which is carrying the patient.

While the invention has been described with reference to exemplary embodiments, it will be understood by those skilled in the art that various changes may be made and equivalents may be substituted for elements thereof without departing from the scope of the invention. Therefore, it is intended that the invention not be limited to the particular embodiment disclosed as the best or only mode contemplated for carrying out this invention, but that the invention will include all embodiments falling within the scope of the appended claims. Furthermore, the use of the terms a, an, etc. do not denote a limitation of quantity, but rather denote the presence of at least one of the referenced item.

What is claimed is:

1. A patient supporting apparatus for imaging and intervention with a medical imaging system, comprising:
    a tabletop having a superior tabletop end coupled to an inferior tabletop end by a bridge tabletop member, the bridge tabletop member having bridge tabletop member width lesser than a tabletop width of each of the superior tabletop and inferior tabletop ends of the tabletop so as to define an open tabletop area between the superior tabletop and inferior tabletop ends of the tabletop;
    a stretcher having a superior stretcher end coupled to an inferior stretcher end by a bridge stretcher member, the bridge stretcher member having a bridge stretcher width less than a stretcher width of each of the superior stretcher and inferior stretcher ends of the stretcher so as to define an open stretcher area between the superior stretcher and inferior stretcher ends of the stretcher, the tabletop movably engaged to the stretcher such that in at least one position the open tabletop area and open stretcher area are in alignment to provide access to a body part of a patient lying in a supine position on the tabletop;
    a fixation member located proximate to the open tabletop area having a guidance plate for receiving a medical device, the fixation member removably coupled to the tabletop and adjustable relative to the tabletop for positioning the guidance plate near the pelvic region of the patient; and
    the tabletop movable relative to the stretcher for insertion of the tabletop into a bore of the medical imaging system.

2. The apparatus of claim 1, wherein the bridge tabletop member width is less than half the tabletop width of one of the superior and inferior ends of the tabletop and at least 0.3 meters in length.

3. The apparatus of claim 1, wherein the bridge tabletop member extends along an axis offset from a centerline of the tabletop extending between the superior and inferior ends of the tabletop.

4. The apparatus of claim 1, wherein the bridge tabletop member is arcuate in a plane perpendicular to a plane defining the width of the superior tabletop and inferior tabletop ends of the tabletop.

5. The apparatus of claim 1, wherein the open tabletop area opens to a side of the tabletop.

6. The apparatus of claim 1, wherein the bridge tabletop member is movable relative to the superior tabletop and inferior tabletop ends of the tabletop.

7. The apparatus of claim 1, wherein the bridge stretcher member is movable relative to the superior stretcher and inferior stretcher ends of the stretcher.

8. The apparatus of claim 1, wherein the guidance plate comprises an array of openings for receiving the medical device.

9. The apparatus of claim 8, further comprising a second guidance plate mounted to the fixation member, the second guidance plate having a second array of openings for receiving the medical device, wherein at least one of the guidance plate and second guidance plate is connected to an actuator for moving the at least one of the guidance plate and second guidance plate relative to each other to displace the array of openings therein for securing the medical device received therethrough.

10. The apparatus of claim 1, further comprising a pair of adjustable leg supports affixed to the tabletop, each of the pair of adjustable leg support for receiving a leg of the patient and each of the pair of adjustable leg supports is movable relative to the other of the pair of adjustable leg supports.

11. The apparatus of claim 10, wherein each of the pair of adjustable leg supports further comprises a locking means for locking its position relative the other of the pair of adjustable leg supports and a restraining means for restraining a leg of the patient.

12. The apparatus of claim 10, wherein the tabletop further comprises an arm support for maintaining a position of an arm of the patient at a side of the patient.

13. The apparatus of claim 12, further comprising an adjustable head rest connected to the superior tabletop end.

14. The apparatus of claim 1, further comprising a patient supporting surface removably engaged with the tabletop to raise a pelvis of the patient towards a central axis of the bore of the medical imaging system when the tabletop is inserted therein.

15. The apparatus of claim 1, wherein the tabletop further comprises a cutout for receiving a magnetic resonance imaging coil.

16. The apparatus of claim 15, further comprising a magnetic resonance imaging coil engaged to the guidance plate.

17. The apparatus of claim 1, wherein the fixation member is an adjustable arm movably coupled the tabletop via a superior-inferior slider.

18. The apparatus of claim 17, wherein the fixation member further comprises a rotating ball joint for adjustment of the fixation member relative to the tabletop.

19. The apparatus of claim 18, wherein the fixation member further comprises locking means for securing the position of the fixation member and the guidance plate thereon.

20. A medical imaging system, comprising:
    an imager for acquiring data used to generate a multidimensional image of an area of interest of a patient, the imager having an access opening in communication with an imaging volume;
    a patient supporting apparatus having:
        a tabletop having a superior tabletop end coupled to an inferior tabletop end by a bridge tabletop member, the bridge tabletop member having bridge tabletop member width lesser than a tabletop width of each of the superior tabletop and inferior tabletop ends of the tabletop so as to define an open tabletop area between the superior tabletop and inferior tabletop ends of the tabletop; and
        a stretcher having a superior stretcher end coupled to an inferior stretcher end by a bridge stretcher member, the bridge stretcher member having a bridge stretcher width less than a stretcher width of each of the superior stretcher and inferior stretcher ends of the stretcher so as to define an open stretcher area between the superior stretcher and inferior stretcher ends of the stretcher, the tabletop movably engaged to the stretcher such that in at least one position the open tabletop area and open stretcher area are in alignment to provide access to a body part of a patient lying in a supine position on the tabletop;

a fixation member located proximate to the open tabletop area having a guidance plate for receiving a medical device, the fixation member removably coupled to the tabletop and adjustable relative to the tabletop for positioning the guidance plate near the pelvic region of the patient; and the tabletop movable relative to the stretcher for insertion of the tabletop into the access opening of the imager.

\* \* \* \* \*